US012721583B2

(12) United States Patent
Kang et al.

(10) Patent No.: US 12,721,583 B2
(45) Date of Patent: Sep. 1, 2026

(54) COMPUTED TOMOGRAPHY IMAGE ANALYSIS DEVICE AND ANALYSIS METHOD USING SAME

(71) Applicant: MEDITULIP CO., LTD., Cheongju-si (KR)

(72) Inventors: Min Woong Kang, Daejeon (KR); Ji Eun Oh, Daejeon (KR)

(73) Assignee: MEDITULIP CO., LTD., Cheongju-si (KR)

( * ) Notice: Subject to any disclaimer, the term of this patent is extended or adjusted under 35 U.S.C. 154(b) by 259 days.

(21) Appl. No.: 18/720,386

(22) PCT Filed: Dec. 7, 2022

(86) PCT No.: PCT/KR2022/019795
§ 371 (c)(1),
(2) Date: Jul. 25, 2024

(87) PCT Pub. No.: WO2023/113358
PCT Pub. Date: Jun. 22, 2023

(65) Prior Publication Data

US 2025/0082291 A1 Mar. 13, 2025

(30) Foreign Application Priority Data

Dec. 15, 2021 (KR) ........................ 10-2021-0180172

(51) Int. Cl.
*A61B 6/00* (2024.01)
*A61B 6/03* (2006.01)
(Continued)

(52) U.S. Cl.
CPC .............. *A61B 6/5217* (2013.01); *A61B 6/03* (2013.01); *G06T 7/0012* (2013.01); *G06T 7/62* (2017.01);
(Continued)

(58) Field of Classification Search
CPC ........... A61B 6/5217; A61B 6/03; G06T 7/62; G06T 7/0012; G06T 2207/10081;
(Continued)

(56) References Cited

U.S. PATENT DOCUMENTS

2022/0383501 A1* 12/2022 Ohno .................... G06T 7/0016

FOREIGN PATENT DOCUMENTS

CN 109288536 B 1/2021
KR 10-2010-0071595 A 6/2010
(Continued)

*Primary Examiner* — Ming Shui
(74) *Attorney, Agent, or Firm* — Bridgeway IP Law Group, PLLC; Jihun Kim

(57) ABSTRACT

An embodiment provides a computed tomography image analysis device and an analysis method using same, the computed tomography image analysis device comprising: a parameter calculation unit that, on the basis of the volume of a lesion in a computed tomography image and a histogram showing the distribution of Hounsfield values, calculates a reference value for the Hounsfield values; an excess rate calculation unit that calculates an excess rate that corresponds to the ratio of a region with a Hounsfield value exceeding the reference value to the total volume of the lesion in the computed tomography image; and a prediction value calculation unit that, on the basis of whether or not the excess rate exceeds a cutoff value on a reference ROC curve for the reference value, calculates a prediction value regarding whether the lesion is invasive or not.

13 Claims, 5 Drawing Sheets

(51) Int. Cl.
*G06T 7/00* (2017.01)
*G06T 7/62* (2017.01)
*G16H 50/20* (2018.01)

(52) U.S. Cl.
CPC ... *G16H 50/20* (2018.01); *G06T 2207/10081* (2013.01); *G06T 2207/20076* (2013.01); *G06T 2207/30096* (2013.01)

(58) Field of Classification Search
CPC G06T 2207/20076; G06T 2207/30096; G16H 50/20
See application file for complete search history.

(56) References Cited

FOREIGN PATENT DOCUMENTS

| | | | | |
|---|---|---|---|---|
| KR | 10-2016-0120707 A | | 10/2016 | |
| KR | 10-2035381 B1 | | 10/2019 | |
| KR | 10-2045435 B1 | | 12/2019 | |
| WO | 2015-183934 A1 | | 12/2015 | |
| WO | WO-2023285993 A1 | * | 1/2023 | ............... A61B 6/50 |

* cited by examiner

COMPUTED TOMOGRAPHY IMAGE ANALYSIS DEVICE AND ANALYSIS METHOD USING SAME

TECHNICAL FIELD

The present invention relates to a computed tomography image analysis device and an analysis method using the same, and more specifically, to a computed tomography image analysis device capable of simply and accurately predicting whether a lesion is invasive based on the ratio of an area in which the Hounsfield value exceeds a reference value among the entire volume of the lesion in a computed tomography image, and an analysis method using the same.

BACKGROUND ART

Recently, as computed tomography (CT) examinations for early detection of lung cancer have become widespread, the rate of lesions appearing in the form of ground-glass opacity (GGO) being discovered through imaging examinations such as chest CT has been continuously increasing.

Ground-glass opacity nodules refer to ground-glass opacity that appears in the shape of round nodules, and may be classified into mixed ground-glass opacity nodules (Part-Solid Ground-Glass Nodules) containing solid components and pure ground-glass opacity nodules (Pure Ground-Glass Nodules, pGGNs) depending on whether solid components exist inside.

Pure ground-glass opacity nodules may be divided into non-invasive adenocarcinoma and invasive adenocarcinoma, and the treatment method may vary depending on the invasiveness.

Since pure ground-glass opacity nodules do not show solid components in the image window setting for observing the lung and mediastinum, the Hounsfield (HU) value corresponding to the brightness value of a computed tomography image for the lesion shows a relatively uniform characteristic. As a result, it is difficult to predict the invasiveness of the lesion with only the simple Hounsfield (HU) value for a computed tomography image.

Recently, the size, volume, shape, and the like of a ground-glass opacity nodule have been known as major computed tomography image features, but when the size of the lesion is small, the correlation between these computed tomography image features and the invasiveness of the lesion has been confirmed to be low. In addition, when the size of a ground-glass opacity nodule is small, the mean, variance, and maximum values of the Hounsfield values of the lesion have been confirmed to have a low correlation with the invasiveness of the lesion.

As a related art document, there is Korean Patent Publication No. 10-2035381 (publication date: Oct. 22, 2019).

DETAILED DESCRIPTION OF THE INVENTION

Technical Problem

An aspect of the present invention is to provide a computed tomography image analysis device capable of simply and accurately predicting whether a lesion is invasive based on the ratio of an area in which the Hounsfield value exceeds a reference value among the entire volume of the lesion in a computed tomography image, and an analysis method using the same.

The aspect of the present invention is not limited to that mentioned above, and other aspects not mentioned will be clearly understood by those skilled in the art from the description below.

Technical Solution

To this end, the present invention provides a computed tomography image analysis device including: a parameter calculation unit for calculating a reference value for a Hounsfield value based on a histogram representing the distribution of the Hounsfield value and the volume of a lesion in a computed tomography image; an excess rate calculation unit for calculating an excess rate corresponding to a ratio of an area in which the Hounsfield value exceeds the reference value among the entire volume of the lesion in the computed tomography image; and a prediction value calculation unit for calculating a prediction value regarding whether the lesion is invasive based on whether the excess rate exceeds a cutoff value on a reference ROC curve for the reference value.

The excess rate calculation unit may calculate the excess rate using Mathematical Equation 1 below.

$$\gamma = \frac{V_H}{(V_H + V_L)} \times 100[\%] \quad \text{[Mathematical Equation 1]}$$

$\gamma$ represents the excess rate, $V_H$ represents the volume of the area in the lesion where the Hounsfield value is greater than the reference value, and $V_L$ represents the volume of the area in the lesion where the Hounsfield value is less than the reference value.

The parameter calculation unit may calculate a cutoff value candidate with the maximum Youden function among cutoff value candidates on the reference ROC curve as the cutoff value.

In addition, the parameter calculation unit may select a plurality of reference value candidates related to the reference value on the histogram, calculate each excess rate candidate value for each of the plurality of reference value candidates using [Mathematical Equation 1], generate a candidate ROC curve for each of the excess rate candidate values, and then select, among the excess rate candidate values, a reference value candidate where the area under the curve for the candidate ROC curve is the largest as the reference value.

The prediction value calculation unit may calculate the accuracy of the prediction value using Mathematical Equation 2 and Mathematical Equation 3 below.

$$P_I = \frac{P_r[H_i = 1, \gamma]}{P_r[H_i = 1, \gamma] + P_r[H_i = 0, \gamma]} \times 100 \quad \text{[Mathematical Equation 2]}$$

$$P_{nI} = \frac{P_r[H_i = 0, \gamma]}{P_r[H_i = 1, \gamma] + P_r[H_i = 0, \gamma]} \times 100 \quad \text{[Mathematical Equation 3]}$$

$P_I$ represents invasive accuracy, $P_{nI}$ represents non-invasive accuracy, $P_r[H_i=1,\gamma]$ represents an invasiveness probability value corresponding to a case where the lesion is invasive for the excess rate ($\gamma$), and $P_r[H_i=0,\gamma]$ represents a non-invasiveness probability value corresponding to a case where the lesion is non-invasive for the excess rate ($\gamma$).

In addition, the parameter calculation unit may calculate a modeling graph based on the empirical joint probability distribution of the actual excess rate and actual invasiveness for the lesion, and, on the modeling graph, calculate the invasiveness probability value corresponding to a case where the lesion is invasive for the excess rate, and the non-invasiveness probability value corresponding to a case where the lesion is non-invasive, to transmit the results to the prediction value calculation unit.

In addition, the parameter calculation unit may update the reference value and the cutoff value based on a new computed tomography image when the new computed tomography image is input from the outside.

In addition, the parameter calculation unit may update the modeling graph based on a pathological actual value for the invasiveness of the lesion identified from the previous computed tomography image, and update the invasiveness probability value and the non-invasiveness probability value based on the newly updated modeling graph.

According to another embodiment of the present invention, the present invention provides a computed tomography image analysis method for analyzing a computed tomography image using the above-described computed tomography image analysis device, including: a reference value calculation step in which the parameter calculation unit calculates the reference value based on a histogram representing the distribution of the Hounsfield value and the volume of the lesion; an excess rate calculation step in which the excess rate calculation unit calculates an excess rate corresponding to the ratio of an area in which the Hounsfield value exceeds the reference value among the entire volume of the lesion; and a prediction value calculation step in which the prediction value calculation unit calculates a prediction value regarding whether the lesion is invasive based on whether the excess rate exceeds a cutoff value on a reference ROC curve for the reference value.

The computed tomography image analysis method may further include a cutoff value calculation step in which the parameter calculation unit calculates the cutoff value.

In the cutoff value calculation step, the parameter calculation unit may select a cutoff value candidate having a maximum Youden function among cutoff value candidates on the reference ROC curve as the cutoff value.

The reference value calculation step may include: a histogram calculation step in which the parameter calculation unit represents the distribution of the Hounsfield value and the volume of the lesion as a histogram; a reference value candidate selection step in which the parameter calculation unit selects a plurality of reference value candidates related to the reference value on the histogram; a step in which the parameter calculation unit calculates excess rate candidate values using [Mathematical Equation 1] for the plurality of reference value candidates, respectively; a curve generation step in which the parameter calculation unit generates a candidate ROC curve for each of the excess rate candidate values; and a reference value selection step in which the parameter calculation unit selects a reference value candidate that has the largest area under the curve for the candidate ROC curve among the respective excess rate candidate values as the reference value.

In addition, the computed tomography image analysis method may further include a probability value calculation step in which the parameter calculation unit calculates a modeling graph modeled based on the empirical joint probability distribution of the actual excess rate and actual invasiveness for the lesion, and calculates the invasiveness probability value corresponding to a case where the lesion is invasive and the non-invasiveness probability value corresponding to a case where the lesion is non-invasive on the modeling graph for the excess rate.

In addition, the computed tomography image analysis method may further include an accuracy calculation step in which the prediction value calculation unit calculates the accuracy of the prediction value based on the invasiveness probability value and non-invasiveness probability value received from the parameter calculation unit.

In addition, the computed tomography image analysis method may further include a learning step in which the parameter calculation unit updates the reference value and the cutoff value based on a new computed tomography image input from outside.

In the learning step, the parameter calculation unit may update the modeling graph based on a pathological actual value for the invasiveness of the lesion identified from the previous computed tomography image, and update the invasiveness probability value and the non-invasiveness probability value based on the newly updated modeling graph.

Advantageous Effects

The computed tomography image analysis device and the analysis method using the same according to the present invention have the advantage in that an excess rate corresponding to the ratio of an area in which the Hounsfield value exceeds a reference value among the entire volume of the lesion in a computed tomography image is calculated, and it is possible to simply and accurately predict whether the lesion is invasive based on whether the excess rate exceeds a cutoff value on a reference ROC curve for the reference value.

In addition, the computed tomography image analysis device and the analysis method using the same according to the present invention have the advantage of further improving the accuracy of determining whether a newly input computed tomography image is invasive through a learning process using an invasiveness probability value and a non-invasiveness probability value updated based on pathological actual values for the invasiveness of the lesion.

The effects of the present invention are not limited to the effects described above, and should be understood to include all effects that are inferable from the configuration of the present invention described in the detailed description or claims of the present invention.

MODE FOR CARRYING OUT THE INVENTION

Hereinafter, preferred embodiments of the present invention, in which it is possible to achieve aspects described above, are described with reference to the accompanying drawings. In describing the embodiments, the same names and symbols are used for the same components, and additional descriptions thereof are omitted below.

Throughout the specification, when a portion is said to be "connected (linked, contacted, combined)" with another portion, this includes not only a case of being "directly connected" but also a case of being "indirectly connected" with another member in between. In addition, when a portion is said to "include" a certain component, this does not mean that other components are excluded, but that other components may be added, unless specifically stated to the contrary.

The terms used herein are merely used to describe specific embodiments and are not intended to limit the present invention. Singular expressions include plural expressions unless the context clearly dictates otherwise. In this specification, it should be understood terms such as "include" or "have" are to designate the presence of features, numbers, steps, operations, components, parts, or combinations thereof described in the specification, but are not to exclude in advance the possibility of the presence or addition of one or more other features, numbers, steps, operations, components, parts, or combinations thereof.

The present invention may be used for predicting the invasiveness of a lesion, which is a pathological result, by using features extracted from a computed tomography image before surgery. The lesion mentioned in the present invention includes a pure ground-glass opacity nodule, and an image of the pure ground-glass opacity nodule may be obtained from a three-dimensional computed tomography image of the chest.

Referring to FIGS. 1 to 6, a computed tomography image analysis device according to an embodiment of the present invention and an analysis method using the same will be described as follows.

A computed tomography image analysis device according to the present embodiment may include an excess rate calculation unit 100, a prediction value calculation unit 200, and a parameter calculation unit 300.

The parameter calculation unit 300 calculates a reference value ($\theta_{HU}$) for a Hounsfield value based on a histogram representing the distribution of the Hounsfield value and the volume of the lesion in a computed tomography image.

A process of calculating the reference value ($\theta_{HU}$) by the parameter calculation unit 300 is as follows.

Figure 1:
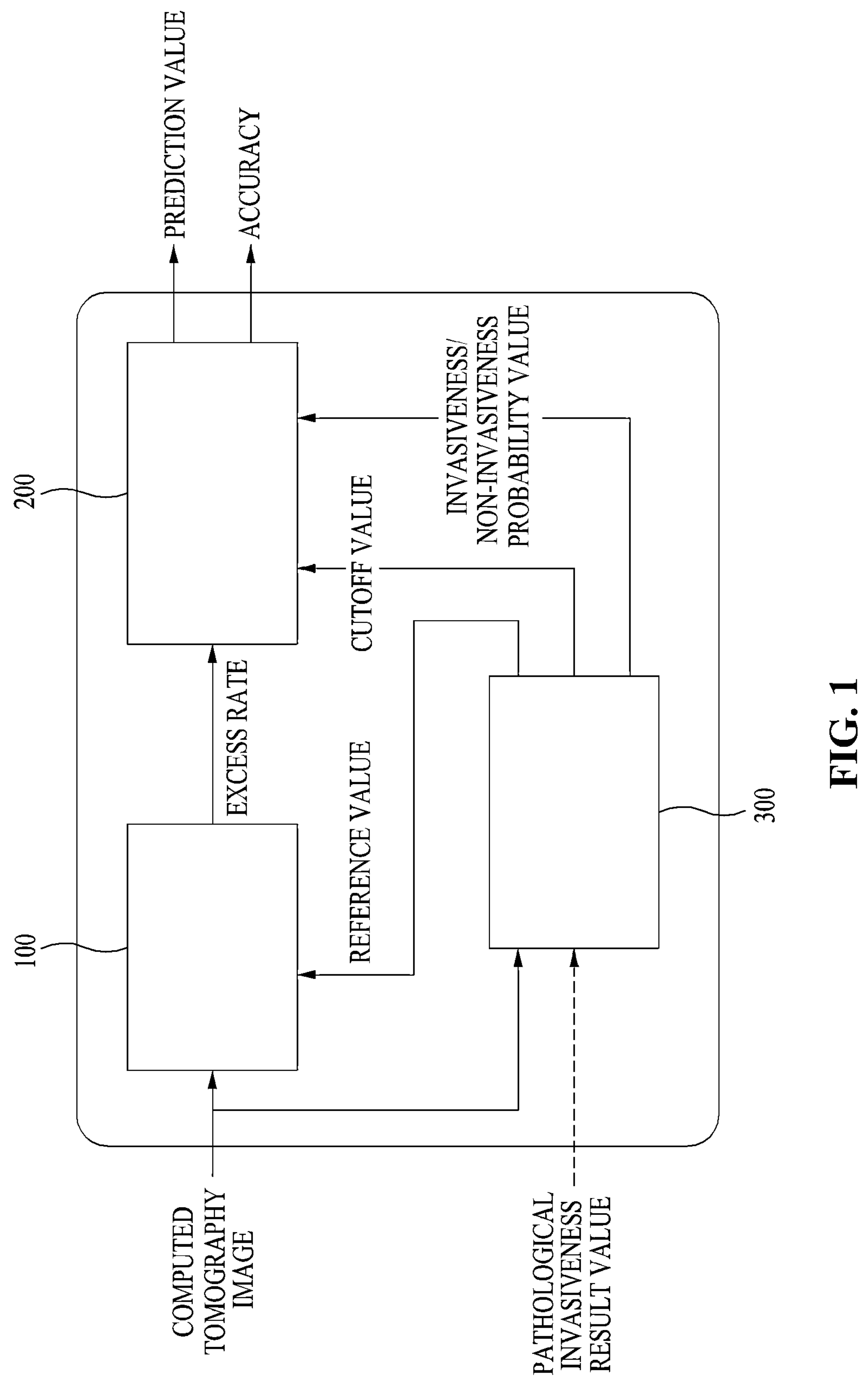
FIG. 1 is a block diagram showing the structure of a computed tomography image analysis device according to the present invention.
Figure 2:
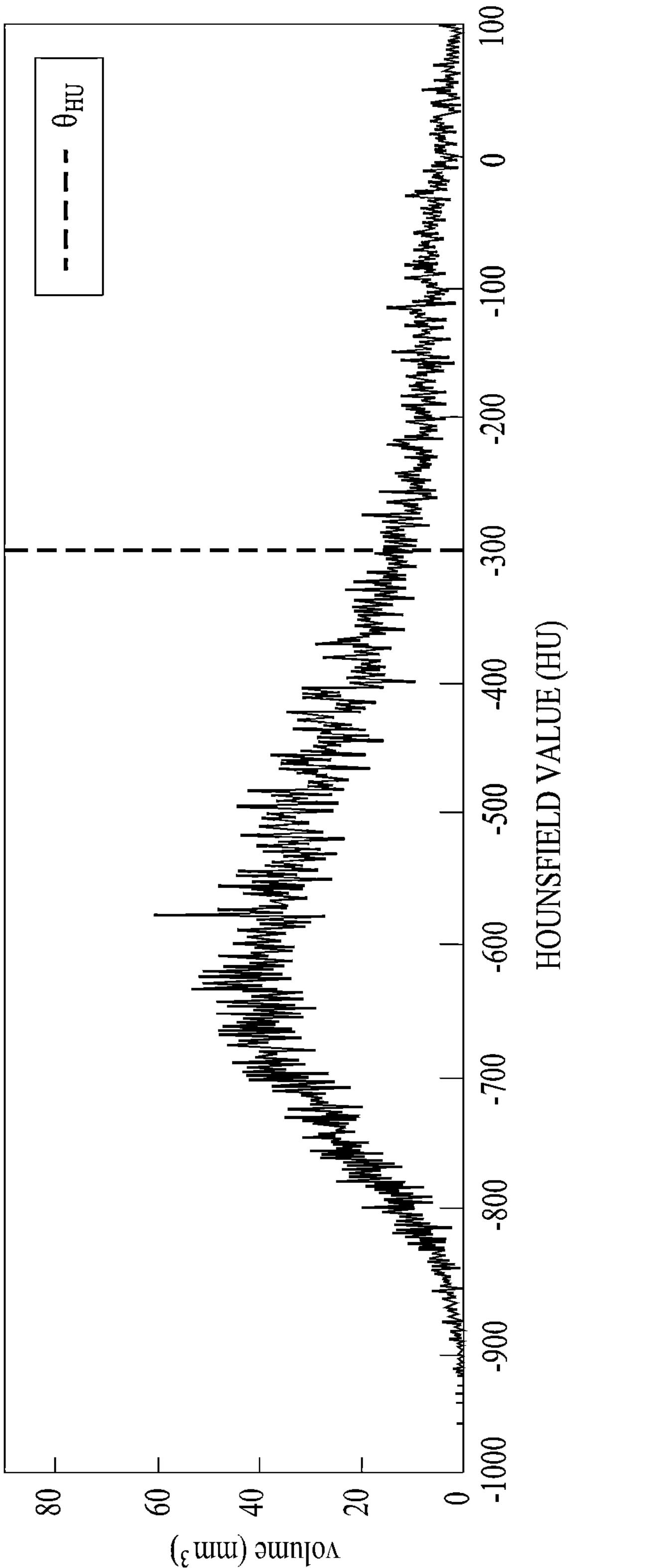
FIG. 2 is a view showing a histogram of the Hounsfield value of a pure ground-glass opacity nodule.

First, when the parameter calculation unit 300 receives a file in the form of Digital Imaging and Communication in Medicine (DICOM) for the lesion from the outside, the distribution of the Hounsfield value of a computed tomography (CT) image and the volume for the lesion is obtained in the form of a histogram, as shown in FIG. 2. That is, the parameter calculation unit 300 expresses the distribution of the Hounsfield value and the volume of the lesion as a histogram.

Here, DICOM refers to a standard used when expressing digital image data in medical devices or during communication using digital image data. FIG. 2 shows a case where the reference value ($\theta_{HU}$) is −300 HU on the histogram.

Next, the parameter calculation unit 300 selects multiple reference value candidates related to the reference value ($\theta_{HU}$) on the histogram. Referring to FIG. 2, in this embodiment, reference value candidates may be selected from the range of Hounsfield values shown on the histogram, that is, from −1000 HU to 100 HU.

Preferably, reference value candidates may be selected within the range where high Hounsfield values in the lesion are distributed on average. For example, the parameter calculation unit 300 may select the reference value candidates based on the range where previous reference values having been selected from previously stored computed tomography images are distributed. In this embodiment, with reference to FIG. 2, the reference value candidates are selected from −500 HU to 100 HU, and the interval between the reference candidate values is set to 50.

Next, the parameter calculation unit 300 calculates excess rate candidate values using [Mathematical Equation 1] for the reference value candidates, respectively.

Next, the parameter calculation unit 300 generates a candidate ROC curve for each excess rate candidate value.

Figure 3:
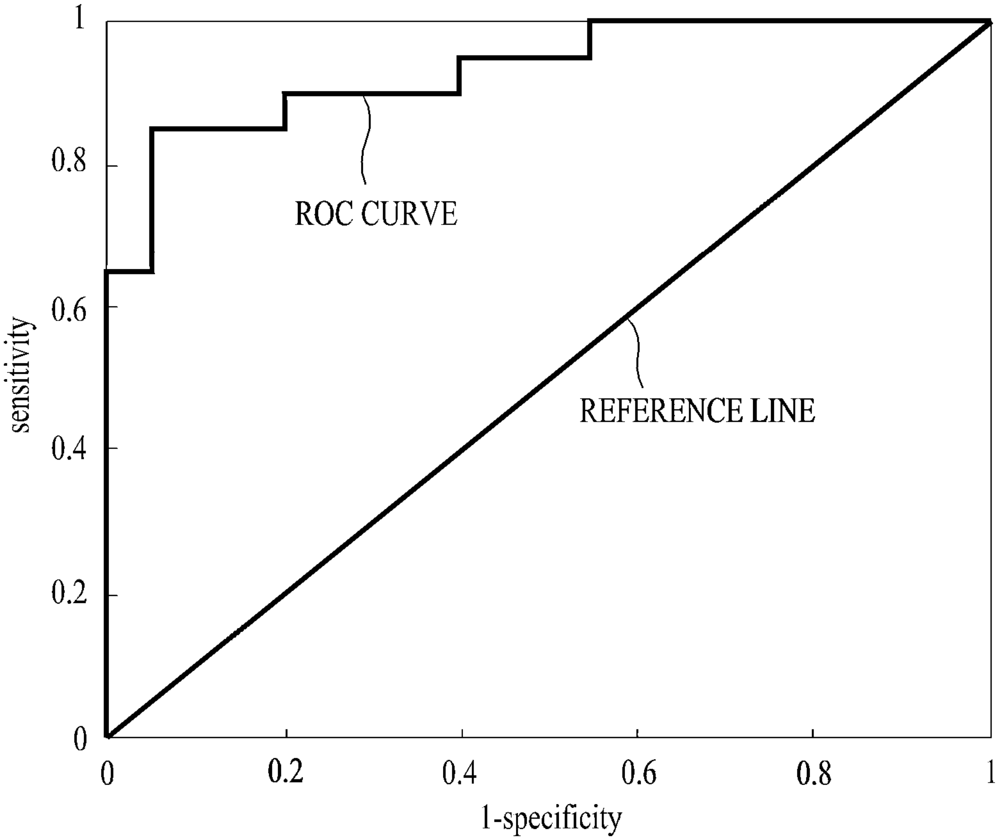
FIG. 3 is a view showing an example of an ROC curve with sensitivity and specificity according to an excess rate as the axes.

FIG. 3 is a view showing an example of a candidate ROC curve with sensitivity and specificity (1-Specificity) as axes for an excess rate candidate value when lesions are classified into invasive and non-invasive. Referring to FIG. 3, it is possible to see that the candidate ROC curve is in the upper area of the reference line.

Next, the parameter calculation unit 300 selects a reference value candidate that has the maximum area under the curve (AUC: Area Under ROC Curve) for the candidate ROC curve among excess rate candidate values as a reference value.

Figure 4:
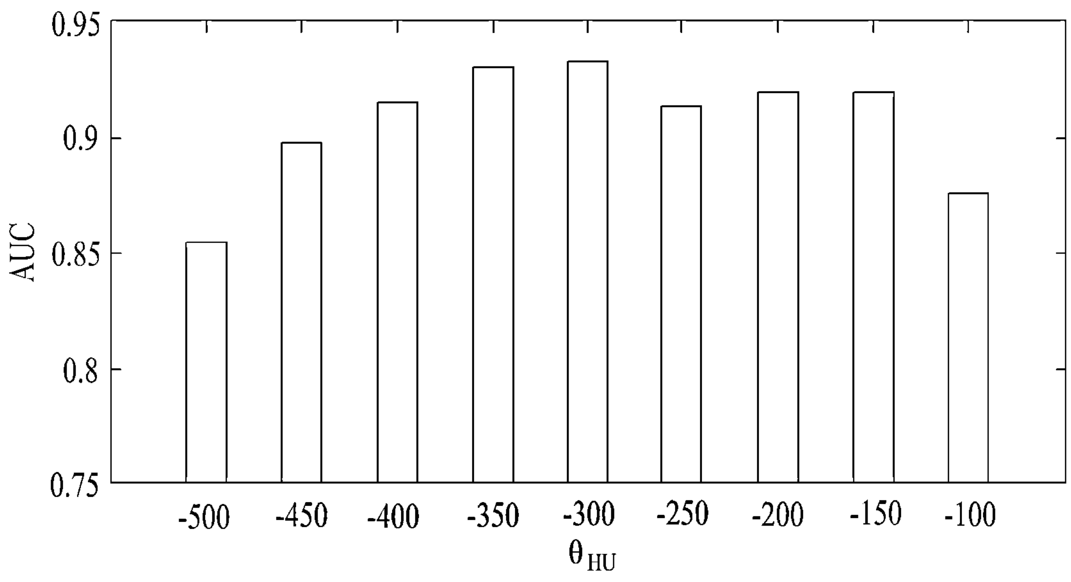
FIG. 4 is a graph comparing the area under an ROC curve for reference value candidates.

FIG. 4 is an example of a graph comparing the area under the curve (AUC) for the candidate ROC curve for excess rate candidate values. Referring to FIG. 4, in this embodiment, −300 HU, which has the maximum area under the curve (AUC), is selected as a reference value.

Meanwhile, the excess rate calculation unit 100 may calculate an excess rate ($\gamma$) corresponding to the ratio of the area in an input computed tomography image for the lesion in which the Hounsfield value exceeds a reference value ($\theta_{HU}$) calculated by the parameter calculation unit 30) among the total volume of the lesion.

The excess rate ($\gamma$) may be calculated by Mathematical Equation 1 below.

$$\gamma = \frac{V_H}{(V_H + V_L)} \times 100[\%] \quad \text{[Mathematical Equation 1]}$$

Here, $\gamma$ represents the excess rate, $V_H$ represents the volume of the area in the lesion where the Hounsfield value is greater than the reference value ($\theta_{HU}$), and $V_L$ represents the volume of the area in the lesion where the Hounsfield value is less than the reference value ($\theta_{HU}$).

In addition, $V_H$ and $V_L$ are obtained from a graph that represents the distribution of the Hounsfield value and the volume for the lesions in the form of a histogram. For example, in the histogram shown in FIG. 2, based on the reference value ($\theta_{HU}$), $V_H$ corresponds to the area under the graph where the Hounsfield value is greater than the reference value ($\theta_{HU}$), and $V_L$ corresponds to the area under the graph where the Hounsfield value is less than the reference value ($\theta_{HU}$).

The excess rate calculation unit 100 receives the reference value ($\theta_{HU}$) from the parameter calculation unit 300 and calculates the excess rate ($\gamma$) according to [Mathematical Equation 1].

Meanwhile, the prediction value calculation unit 200 may calculate, based on whether an excess rate ($\gamma$) exceeds a cutoff value ($\theta_\gamma$) on a reference Receiver Operating Characteristic (ROC) curve for a reference value (θHU), a prediction value $(H_i^p)$.

The prediction value calculation unit 200 may output the prediction value as 1 if the excess rate (γ) is greater than or equal to the cutoff value ($\theta_\gamma$), and output the prediction value as 0 if the excess rate (γ) is less than the cutoff value ($\theta_\gamma$).

Here, if the prediction value $(H_i^p)$ is 1, the lesion is invasive, and if the prediction value $(H_i^p)$ is 0, the lesion is non-invasive.

The prediction value calculation unit 200 receives the cutoff value ($\gamma_\gamma$) from the parameter calculation unit 300.

A process in which the parameter calculation unit 300 calculates the cutoff value ($\theta_\gamma$) is as follows.

The parameter calculation unit 300 calculates the Youden function values for all cutoff value candidates on a reference ROC curve for a selected reference value. Since the Youden function value is a value calculated through the Youden's Index, a detailed description thereof is omitted.

Figure 5:
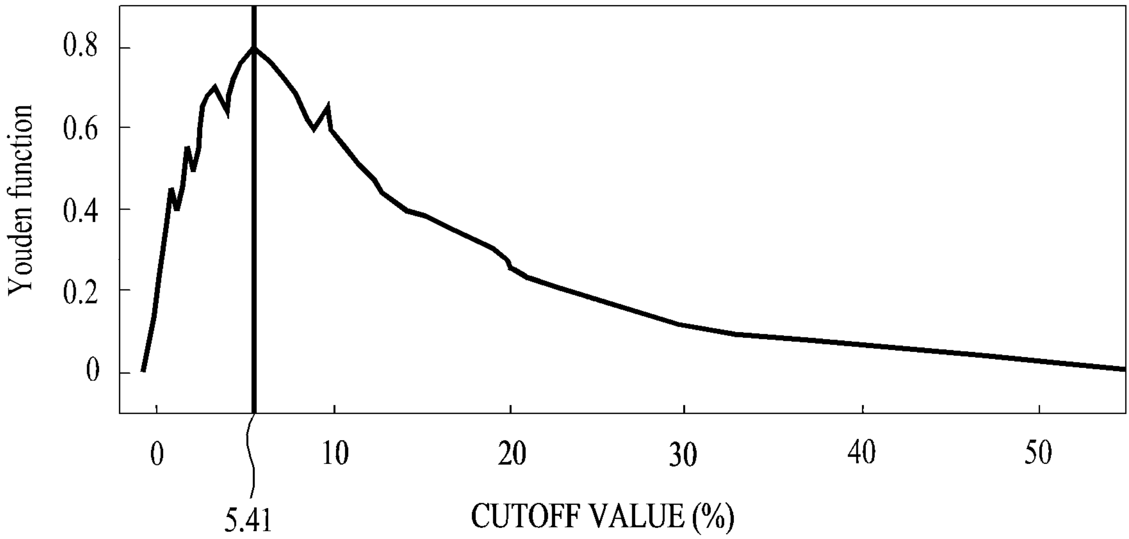
FIG. 5 is a view showing the value of the Youden function with sensitivity and specificity as variables for possible cutoff values in an ROC curve.

The parameter calculation unit 300 selects a cutoff value candidate that has the maximum Youden function value as the cutoff value ($\theta_\gamma$). Referring to FIG. 5, 5.41% is selected as the cutoff value in this embodiment.

Meanwhile, the prediction value calculation unit 200 may calculate the accuracy of a prediction value corresponding to the difference between the excess rate (γ) and the cutoff value ($\theta_\gamma$).

The accuracy of the prediction value includes invasive accuracy ($P_I$) when the excess rate (γ) is greater than or equal to the cutoff value ($\theta_\gamma$), and non-invasive accuracy (P nI) when the excess rate (γ) is less than the cutoff value ($\theta_\gamma$).

The invasive accuracy ($P_I$) is calculated by [Mathematical Equation 2], and the non-invasive accuracy ($P_{nI}$) is calculated by [Mathematical Equation 3].

$$P_I = \frac{P_r[H_i = 1, \gamma]}{P_r[H_i = 1, \gamma] + P_r[H_i = 0, \gamma]} \times 100 \quad \text{[Mathematical Equation 2]}$$

$$P_{nI} = \frac{P_r[H_i = 0, \gamma]}{P_r[H_i = 1, \gamma] + P_r[H_i = 0, \gamma]} \times 100 \quad \text{[Mathematical Equation 3]}$$

Here, $P_r[H_i=1,\gamma]$ means an invasiveness probability value corresponding to a case where the lesion is invasive for the excess rate (γ), and $P_r[H_i=0,\gamma]$ means a non-invasiveness probability value corresponding to a case where the lesion is non-invasive for the excess rate (γ).

The invasive accuracy ($P_I$) and non-invasive accuracy ($P_{nI}$) have values ranging from 0 to 100, and the quantitative numerical values for the accuracy of the prediction value $(H_i^p)$ are expressed as percentiles.

As the excess rate (γ) has a value greater than the cutoff value ($\theta_\gamma$), that is, as the difference between the excess rate (γ) and the cutoff value ($\theta_\gamma$) increases, the invasive accuracy ($P_I$) approaches 100, so that the invasive accuracy ($P_I$) increases. In addition, as the excess rate (γ) has a value smaller than the cutoff value ($\theta_\gamma$), that is, as the difference between the excess rate (γ) and the cutoff value ($\theta_\gamma$) increases, the non-invasive accuracy ($P_{nI}$) approaches 100, so that the non-invasive accuracy ($P_{nI}$) increases.

The prediction value calculation unit 200 receives the invasiveness probability value ($P_r[H_i=1,\gamma]$) and non-invasiveness probability value ($P_r[H_i=0,\gamma]$) from the parameter calculation unit 300.

A process in which the parameter calculation unit 300 calculates the invasiveness probability value and non-invasiveness probability value is explained as follows.

The invasiveness probability value (($P_r[H_i=1,\gamma]$) and non-invasiveness probability value ($P_r[H_i=0,\gamma]$) may be obtained from a modeling graph modeled based on the empirical joint probability distribution of the actual invasiveness and the actual excess rate for the lesion.

First, the parameter calculation unit 300 calculates a modeling graph modeled based on the empirical joint probability distribution of the actual invasiveness and the actual excess rate for the lesion.

Figure 6:
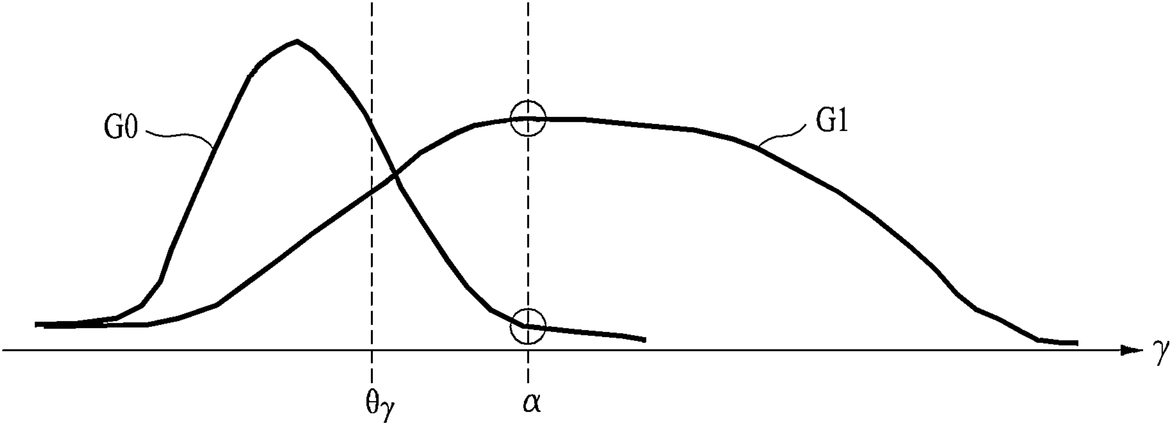
FIG. 6 is a view showing a graph modeling the empirical joint probability distribution between the presence or absence of lesion invasiveness and an excess rate.

As shown in FIG. 6, the modeling graph is a graph obtained through curve fitting based on the actual values of the invasiveness of the lesion obtained from the actual pathological results and the values of the excess rate at that time.

The empirical joint probability distribution satisfies [Mathematical Equation 4], [Mathematical Equation 5], and [Mathematical Equation 6] below.

$$\sum_\gamma P_r[H_i = 0, \gamma] = \frac{N_{nI}}{N_t} \quad \text{[Mathematical Equation 4]}$$

$$\sum_\gamma P_r[H_i = 1, \gamma] = \frac{N_I}{N_t} \quad \text{[Mathematical Equation 5]}$$

$$\sum_{H_i \in (0,1)} \sum_\gamma P_r[H_i = \gamma] = 1 \quad \text{[Mathematical Equation 6]}$$

Here, $N_t$ is the number of collected pure ground-glass opacity nodules, i.e., lesions, and $N_I$ and $N_{nI}$ are the number of lesions classified as invasive adenocarcinoma and non-invasive adenocarcinoma, respectively, among collected lesions.

In FIG. 6, G1 is a curve representing the joint probability distribution according to the excess rate when the lesion is invasive, and G0 is a curve representing the joint probability distribution according to the excess rate when the lesion is non-invasive.

Next, the parameter calculation unit 300 calculates an invasiveness probability value ($P_r[H_i=1,\gamma]$) when the lesion is invasive, and a non-invasiveness probability value ($P_r[H_i=0,\gamma]$) when the lesion is non-invasive, for an excess rate (γ) on a modeling graph.

As shown in FIG. 6, when the value of the excess rate (γ) is α, the invasiveness probability value ($P_r[H_i=1,\gamma]$) is a value corresponding to α in the G1 graph, and the non-invasiveness probability value ($P_r[H_i=0,\gamma]$) is calculated as a value corresponding to α in the G0 graph. Here, the invasiveness probability value ($P_r[H_i=1,\gamma]$) and the non-invasiveness probability value ($P_r[H_i=0,\gamma]$) may each have a value between 0 and 1.

The parameter calculation unit 300 transmits the calculated invasiveness probability value ($P_r[H_i=1,\gamma]$) and non-invasiveness probability value ($P_r[H_i=0,\gamma]$) to the prediction value calculation unit 200.

As a result, when the value of the excess rate (γ) is greater than a cutoff value ($\theta_\gamma$), invasive accuracy ($P_I$) may be output as a value close to 100, and when the excess rate (γ) is near the cutoff value ($\theta_\gamma$), the invasive accuracy ($P_I$) may be output as a value of approximately 50. In this way, the reliability of a prediction value for the invasiveness of the lesion increases as the accuracy for the prediction value is output as a percentile.

Meanwhile, when the parameter calculation unit 300 receives a new computed tomography image from the outside, it is possible to update the reference value and the cutoff value based on the new computed tomography image.

The parameter calculation unit 300 transmits a newly updated reference value to the excess rate calculation unit 100 to which the new computed tomography image is input, and simultaneously transmits a newly updated cutoff value to the prediction value calculation unit 200.

In addition, the parameter calculation unit 300 may update a modeling graph based on a pathological actual value for the invasiveness of the lesion identified in the previous step. For example, the G1 curve and G0 curve of FIG. 6 may be newly set due to the addition of the pathological result for the invasiveness of a new lesion.

The parameter calculation unit 300 may update an invasiveness probability value and a non-invasiveness probability value based on the newly updated modeling graph and transmit the same to the prediction value calculation unit 200.

A process of analyzing a computed tomography image using the above-described computed tomography image analysis device is explained as follows.

First, the parameter calculation unit 300 performs a reference value calculation step of calculating a reference value based on a histogram representing the distribution of the Hounsfield value and the volume of the lesion in a computed tomography image.

When a computed tomography image for the lesion is input to the parameter calculation unit 300, the parameter calculation unit 300 calculates a reference value ($\theta_{HU}$) for calculating an excess rate (γ) and transmits the calculated reference value to the excess rate calculation unit 100.

In the reference value calculation step, the parameter calculation unit 300 first performs a histogram calculation step of representing the distribution of the Hounsfield value and the volume of the lesion as a histogram.

Next, the parameter calculation unit 300 performs a reference value candidate selection step of selecting a plurality of reference value candidates related to the reference value on the histogram.

Next, the parameter calculation unit 300 calculates excess rate candidate values for the plurality of reference value candidates, respectively, using [Mathematical Equation 1].

Next, the parameter calculation unit 300 performs a curve generation step of generating a candidate ROC curve for each of the excess rate candidate values.

Next, the parameter calculation unit 300 performs a reference value selection step of selecting a reference value candidate that has the largest area under the curve for the candidate ROC curve among the respective excess rate candidate values as the reference value.

In addition, the parameter calculation unit 300 calculates the cutoff value ($\theta_\gamma$) based on the reference ROC curve for the reference value ($\theta_{HU}$) and transmits the calculated cutoff value to the prediction value calculation unit 200. That is, a cutoff value calculation step in which the cutoff value is calculated is performed by the parameter calculation unit 300.

In the cutoff value calculation step, a cutoff value candidate with the maximum Youden function among the cutoff value candidates on the reference ROC curve is selected as the cutoff value.

Once a calculation process for the reference value and the cutoff value is completed, the excess rate calculation unit 100 calculates the excess rate (γ) corresponding to the ratio of the area among the entire volume of the lesion in which the Hounsfield value exceeds the reference value in the computed tomography image for the lesion using [Mathematical Equation 1].

Next, the prediction value calculation unit 200 performs a prediction value calculation step of calculating a prediction value regarding the invasiveness of the lesion based on whether the excess rate (γ) exceeds the cutoff value ($\theta_\gamma$) on a reference ROC curve for the reference value.

As a result, the present invention has the advantage of being able to simply and accurately predict the invasiveness of a ground-glass opacity nodule based on the distribution of the Hounsfield value obtainable through image analysis of a three-dimensional chest computed tomography image for a small solid component lung ground-glass opacity nodule.

Next, the parameter calculation unit 300 performs a probability value calculation step of calculating an invasiveness probability value and a non-invasiveness probability value used to calculate the accuracy of the prediction value.

In the probability value calculation step, the parameter calculation unit 300 first performs a graph calculation step of calculating a modeling graph based on the empirical joint probability distribution of the actual invasiveness of the lesion and the actual excess rate.

Next, the parameter calculation unit 300 performs a probability value calculation step of calculating an invasiveness probability value when the lesion is invasive and a non-invasiveness probability value when the lesion is non-invasive, for the excess rate on the modeling graph.

Next, the parameter calculation unit 300 transmits the invasiveness probability value and non-invasiveness probability value to the prediction value calculation unit 200.

Then, the prediction value calculation unit 200 performs an accuracy calculation step of calculating the accuracy of the prediction value based on the invasiveness probability value and non-invasiveness probability value received from the parameter calculation unit 300, while using [Mathematical Equation 2] and [Mathematical Equation 3].

The accuracy of the prediction value may include invasive accuracy when the excess rate is greater than or equal to the cutoff value, and non-invasive accuracy when the excess rate is less than the cutoff value.

Of course, the present invention is not limited thereto, and the prediction value calculation step and the accuracy calculation step may be performed simultaneously.

Meanwhile, the computed tomography image analysis method may further include a learning step in which the parameter calculation unit 300 updates the reference value and the cutoff value based on a new computed tomography image input from the outside.

In the learning step, the parameter calculation unit may update the modeling graph based on a pathological actual value for the invasiveness of the lesion identified from the previous computed tomography image, and update the invasiveness probability value and the non-invasiveness probability value based on the newly updated modeling graph.

As a result, the accuracy of determining whether a newly input computed tomography image is invasive may be further improved through a learning process using an invasiveness probability value and a non-invasiveness probability value updated based on pathological true values for the invasiveness of the lesion identified from the previous computed tomography image.

As described above, the present invention is not limited to specific preferred embodiments described above, and various modifications may be made by those skilled in the art without departing from the feature of the present invention as claimed in the claims, and such modifications fall within the scope of the present invention.

EXPLANATION OF REFERENCE NUMERALS

100: Excess rate calculation unit 200: Prediction value calculation unit

300: Parameter calculation unit

INDUSTRIAL APPLICABILITY

Recently, as computed tomography (CT) examinations for early detection of lung cancer have become widespread, the rate of lesions appearing in the form of ground-glass opacity (GGO) being discovered through imaging examinations such as chest CT has been continuously increasing.

The computed tomography image analysis device and the analysis method using the same according to the present invention are capable of simply and accurately predicting whether a lesion is invasive based on the ratio of an area in which the Hounsfield value exceeds a reference value among the entire volume of the lesion in a computed tomography image, and are thus industrially applicable.

The invention claimed is:

1. A computed tomography image analysis device comprising at least one processor including:

a parameter calculation unit for calculating a reference value for a Hounsfield value based on a histogram representing a distribution of the Hounsfield value and a volume of a lesion in a computed tomography image;

an excess rate calculation unit for calculating an excess rate corresponding to a ratio of an area in which the Hounsfield value exceeds the reference value among the entire volume of the lesion in the computed tomography image; and a prediction value calculation unit for calculating a prediction value regarding whether the lesion is invasive based on whether the excess rate exceeds a cutoff value on a reference ROC curve for the reference value, wherein the excess rate calculation unit calculates the excess rate using Mathematical Equation 1 below, $$\gamma = \frac{V_H}{(V_H + V_L)} \times 100[\%] \quad \text{[Mathematical Equation 1]}$$

wherein, the $\gamma$ represents the excess rate, the $V_H$ represents a volume of the area in the lesion where the Hounsfield value is greater than the reference value, and the $V_L$ represents a volume of the area in the lesion where the Hounsfield value is less than the reference value.

2. The computed tomography image analysis device of claim 1, wherein the parameter calculation unit calculates a cutoff value candidate with the maximum Youden function among cutoff value candidates on the reference ROC curve as the cutoff value.

3. The computed tomography image analysis device of claim 2, wherein the parameter calculation unit selects a plurality of reference value candidates related to the reference value on the histogram, calculates each excess rate candidate value for each of the plurality of reference value candidates using the Mathematical Equation 1, generates a candidate ROC curve for each of excess rate candidate values, and then selects, among the excess rate candidate values, a reference value candidate where the area under a curve for the candidate ROC curve is the largest as the reference value.

4. The computed tomography image analysis device of claim 1, wherein the prediction value calculation unit calculates an accuracy of the prediction value using Mathematical Equation 2 and Mathematical Equation 3 below, $$P_I = \frac{P_r[H_i = 1, \gamma]}{P_r[H_i = 1, \gamma] + P_r[H_i = 0, \gamma]} \times 100 \quad \text{[Mathematical Equation 2]}$$

$$P_{nI} = \frac{P_r[H_i = 0, \gamma]}{P_r[H_i = 1, \gamma] + P_r[H_i = 0, \gamma]} \times 100 \quad \text{[Mathematical Equation 3]}$$

wherein, the $P_1$ represents invasive accuracy, the $P_{nI}$ represents non-invasive accuracy, the $P_r[H_i=1,\gamma]$ represents an invasiveness probability value corresponding to a case where the lesion is invasive for the excess rate ($\gamma$), and the $P_r[H_i=0,\gamma]$ represents a non-invasiveness probability value corresponding to a case where the lesion is non-invasive for the excess rate ($\gamma$).

5. The computed tomography image analysis device of claim 4, wherein the parameter calculation unit calculates a modeling graph based on an empirical joint probability distribution of actual excess rate and actual invasiveness for the lesion, and, on the modeling graph, calculates the invasiveness probability value corresponding to a case where the lesion is invasive for the excess rate, and the non-invasiveness probability value corresponding to a case where the lesion is non-invasive, to transmit results to the prediction value calculation unit.

6. The computed tomography image analysis device of claim 3, wherein the parameter calculation unit updates the reference value and the cutoff value based on a new computed tomography image when the new computed tomography image is input from an outside.

7. The computed tomography image analysis device of claim 5, wherein the parameter calculation unit updates the modeling graph based on a pathological actual value for an invasiveness of the lesion identified from a previous computed tomography image, and updates the invasiveness probability value and the non-invasiveness probability value based on a newly updated modeling graph.

8. A computed tomography image analysis method for analyzing a computed tomography image using the computed tomography image analysis device according to claim 1, the method comprising:

a reference value calculation step in which the parameter calculation unit calculates the reference value based on a histogram representing the distribution of the Hounsfield value and the volume of the lesion;

an excess rate calculation step in which the excess rate calculation unit calculates an excess rate corresponding to the ratio of an area in which the Hounsfield value exceeds the reference value among the entire volume of the lesion; and a prediction value calculation step in which the prediction value calculation unit calculates a prediction value regarding whether the lesion is invasive based on whether the excess rate exceeds a cutoff value on a reference ROC curve for the reference value, wherein the excess rate calculation unit calculates the excess rate using Mathematical Equation 1 below $$\gamma = \frac{V_H}{(V_H + V_L)} \times 100[\%] \quad \text{[Mathematical Equation 1]}$$

wherein, the γ represents the excess rate, the V H represents a volume of the area in the lesion where the Hounsfield value is greater than the reference value, and the V L represents a volume of the area in the lesion where the Hounsfield value is less than the reference value, and wherein the parameter calculation unit updates a modeling graph based on a pathological actual value for an invasiveness of the lesion identified from a previous computed tomography image, and updates an invasiveness probability value and a non-invasiveness probability value based on a newly updated modeling graph.

9. The computed tomography image analysis method of claim 8, further comprising a cutoff value calculation step in which the parameter calculation unit calculates the cutoff value, wherein in the cutoff value calculation step, the parameter calculation unit selects a cutoff value candidate having a maximum Youden function among cutoff value candidates on the reference ROC curve as the cutoff value.

10. The computed tomography image analysis method of claim 8, wherein the reference value calculation step comprises:

a histogram calculation step in which the parameter calculation unit represents the distribution of the Hounsfield value and the volume of the lesion as a histogram;

a reference value candidate selection step in which the parameter calculation unit selects a plurality of reference value candidates related to the reference value on the histogram;

a step in which the parameter calculation unit calculates excess rate candidate values using the Mathematical Equation 1 for the plurality of reference value candidates, respectively;

a curve generation step in which the parameter calculation unit generates a candidate ROC curve for each of the excess rate candidate values; and a reference value selection step in which the parameter calculation unit selects a reference value candidate that has the largest area under a curve for the candidate ROC curve among the respective excess rate candidate values as the reference value.

11. The computed tomography image analysis method of claim 8, further comprising a probability value calculation step in which the parameter calculation unit calculates the modeling graph modeled based on an empirical joint probability distribution of actual excess rate and actual invasiveness for the lesion, and calculates the invasiveness probability value corresponding to a case where the lesion is invasive and the non-invasiveness probability value corresponding to a case where the lesion is non-invasive on the modeling graph for the excess rate.

12. The computed tomography image analysis method of claim 11, further comprising an accuracy calculation step in which the prediction value calculation unit calculates an accuracy of the prediction value based on the invasiveness probability value and non-invasiveness probability value received from the parameter calculation unit.

13. The computed tomography image analysis method of claim 11, further comprising a learning step in which the parameter calculation unit updates the reference value and the cutoff value based on a new computed tomography image input from outside.

* * * * *